(12) United States Patent
Englebienne et al.

(10) Patent No.: US 7,759,086 B2
(45) Date of Patent: Jul. 20, 2010

(54) DIAGNOSTIC METHOD FOR CHRONIC FATIGUE SYNDROME BY MEASURING ELASTASE

(75) Inventors: Patrick Englebienne, Zingem (BE); Kenny De Meirleir, Mechelen (BE); Charles Vincent Herst, Oakland, CA (US)

(73) Assignee: R.E.D. Laboratories, N.V., Zellik (BE)

( * ) Notice: Subject to any disclaimer, the term of this patent is extended or adjusted under 35 U.S.C. 154(b) by 440 days.

(21) Appl. No.: 11/661,888

(22) PCT Filed: Oct. 6, 2004

(86) PCT No.: PCT/BE2004/000141

§ 371 (c)(1),
(2), (4) Date: Dec. 28, 2007

(87) PCT Pub. No.: WO2006/026837

PCT Pub. Date: Mar. 16, 2006

(65) Prior Publication Data

US 2008/0193957 A1    Aug. 14, 2008

Related U.S. Application Data

(60) Provisional application No. 60/607,822, filed on Sep. 7, 2004.

(51) Int. Cl.
*C12Q 1/34* (2006.01)
(52) U.S. Cl. ........................................ 435/18
(58) Field of Classification Search .................... 435/18
See application file for complete search history.

(56) References Cited

U.S. PATENT DOCUMENTS

| 6,080,554 A | 6/2000 | Campine et al. |
| 6,808,936 B1 | 10/2004 | Englebienne et al. |
| 2005/0009202 A1 | 1/2005 | Englebienne et al. |
| 2005/0019756 A1 | 1/2005 | Englebienne et al. |
| 2005/0032770 A1* | 2/2005 | El Bakkouri et al. ........ 514/200 |

OTHER PUBLICATIONS

Torpy D. et al. Association Between Chronic Fatigue Syndrome and the Corticosteroid Binding Globulin Gene ALA SER Polymorphism. Endocrine Research 30(3)417-429, Aug. 2004.*
Demettre E. et al. Ribonuclease L Proteolysis in Peripheral Blood Mononuclear Cells of Chronic Fatigue Syndrome Patients. J of Biological Chemistry 277(38)35746-51, Sep. 2002.*
Demettre E., "Ribonuclease L Proteolysis in Peripheral Blood Mononuclear Cells of Chronic Fatigue Syndrome Patients", J Biol Chem, Sep. 20, 2002; 277(38): 35746.

* cited by examiner

*Primary Examiner*—Ralph Gitomer
(74) *Attorney, Agent, or Firm*—Bret E. Field; Bozicevic, Field & Francis LLP

(57) ABSTRACT

The present invention relates to methods and kits for the diagnosis and confirmation of Chronic Fatigue Syndrome (CFS) by measuring elastase activity in a patient sample, preferably a PBMC sample. The assays of the invention can also be used to characterize CFS, to determine the disease stage, the disease progression, the efficiency of a therapeutic regime and/or to predict the recurrence of possible attacks. The assays of the invention advantageously allow CFS to be distinguished from other CICIDs like MS or RA.

16 Claims, 4 Drawing Sheets

DIAGNOSTIC METHOD FOR CHRONIC FATIGUE SYNDROME BY MEASURING ELASTASE

This application is a national stage application filed under Rule 371 from PCT/BE2004/000141 filed Oct. 6, 2004 which claims benefit of 60/607,822 filed Sep. 7, 2004.

FIELD OF THE INVENTION

The present invention relates to methods and kits for diagnosing Chronic Fatigue Syndrome (CFS), and for distinguishing CFS from other chronic immune or inflammatory diseases (CICIDs) like Multiple Sclerosis (MS) or Rheumatoid Arthritis (RA).

BACKGROUND

Chronic immune and chronic inflammatory diseases (CICIDs) are a group of severe and debilitating diseases that include Multiple Sclerosis (MS), Chronic Fatigue Syndrome (CFS) and Rheumatoid Arthritis (RA) amongst others.

CICIDs are often pleomorphic in their presentation, the severity of symptoms depending on the extent of the disease.

CICIDs can be highly debilitating. Chronic inflammation can lead to the disruption of normal immune functions (through the cleavage of RNase L protein for example). RNase L protein cleavage and decreased levels of RNase L inhibitor (RLI) mRNA have been linked with chronic immune diseases such as MS and CFS.

RNase L is the terminal enzyme in the 2-5A synthetase/RNase L antiviral pathway (for review, see Bastide et al, 2002, in: *Chronic Fatigue Syndrome, a Biological Approach*, CRC Press, Boca Raton Fla., 2002, pp. 1-15). RNase L (as homodimer) is able to degrade viral RNA (to stop the infectious process) and cellular RNA (to cause the removal of the damaged cell by a process known as programmed cell suicide or apoptosis).

RNase L protein fragments may have enzymatic activity but are unregulated as these protein fragments lack the regulatory (i.e., dimeric) sequences that the native enzyme possesses. A dysfunctional immune system cannot respond correctly to further challenges, completing a vicious circle leading to chronic impairment of the immune defense system. In such cases, chronic infections and chronic inflammation may be the result.

The utility of RNase L protein fragments (such as the 37-kDa fragment) as clinical markers for CFS and MS is well documented (see e.g. De Meirleir et al, 2000, *AM. J. Med.* 108:99-105). Tests based on these markers are, however, technically complex.

Aims of the Invention

An aim of the present invention is to provide simple, cheap but accurate tests that allow diagnosis of CFS, confirmation of CFS and advantageously the distinction of CFS from other CICIDs like MS or RA.

SUMMARY OF THE INVENTION

The present invention relates to a method or assay for diagnosing CFS comprising the step of measuring elastase activity in a patient sample.

The method of the invention preferably is an adjunct method for diagnosing CFS. Preferably the test of the invention is performed in combination with at least one second (standard) test for diagnosing a CICID like CFS.

The sample preferably contains enzymatically active elastase (id est the active form of elastase).

Preferably, said sample is depleted from neutrophils.

More preferably, said sample is a PBMC sample.

Even more preferably, said (PBMC) sample comprises more than 90% mononuclear cells such as peripheral blood mononuclear cells (PBMCs), most preferably more than 95% mononuclear cells such as PBMCs.

According to an embodiment of the invention, the step of measuring consists of measuring elastase activity present in monocytes (for instance those present in a PBMC sample).

Advantageously, a method according to the present invention further comprises the steps of
(a) determining the range or amount of reference
(b) comparing said elastase activity measured to said range or amount of reference
(c) determining from step (b) the putative presence, the presence and/or the progression of CFS.

According to an embodiment of the present invention, a relative difference of at least twice, preferably at least thrice the normal range or amount for elastase activity is indicating the presence of CFS.

According to another embodiment of the invention, an absolute elastase activity level in PBMCs of at least about 1,000 units/mg protein is indicating the presence of CFS in a male patient.

According to a further embodiment of the invention, an absolute elastase activity level in PBMCs of at least about 900 units/mg protein is indicating the presence of CFS in a female patient.

Advantageously, the step of measuring elastase activity consists of measuring digestion of an elastase-substrate.

The elastase-substrate can be a substrate that is naturally present in the sample to assay. Alternatively, the substrate can be added to said sample.

Advantageously, an elastase-substrate is selected from the group consisting of elastin, RNase L, cytokeratin 18, collagen, proteoglycan, thrombomodulin, cadoherins and fibronectin.

Advantageously, protease inhibitors can be added to said sample to inhibit interfering serine proteases.

According to an embodiment of the present invention, the (elastase) method or assay further comprises the step of comparing the results obtained by a method according to the invention with those obtained by a at least one second (standard) method. Preferably said second method is a standard method for diagnosing a CICID like for instance CFS.

Advantageously, said second (standard) method comprises the step of assaying a patient sample for the presence of low molecular weight RNase L fragments (also referred to as an RNase L assay or RNase L fragmentation assay).

Advantageously, a method according to the invention is used to confirm an earlier CFS diagnosis; to characterize CFS; to determine a CFS disease stage and/or its progression; to predict possible attacks; and/or to monitor the efficiency of a CFS therapeutic regimen.

Advantageously, a method according to the present invention, when used or performed in combination with at least one second (standard) method for diagnosing a CICID, allows for the conclusive diagnosis of CFS. Such second assay can refer to an RNase L assay or can refer to a physical exam and the observation of clinical symptoms.

Advantageously, a method according to the present invention, when used or performed in combination with at least one second (standard) method for diagnosing a CICID, allows to distinguish CFS from other CICIDs like MS or RA.

Another aspect of the invention concerns a kit for performing a method according to the invention. Advantageously, said kit comprises means for isolating PBMCs and/or at least one elastase-substrate.

DESCRIPTION OF THE INVENTION

Recently, it has been determined that elastase can cleave Ribonuclease L (RNase L) protein (Demettre et al, 2002, *J of Biol Chem* 277:35764-35751).

Elastase, a member of the serine protease family subgroup, is known to possess broad proteolytic activity (Dallegri et al, 1997, *Inflamm. Res.* 46:383-391). Elastase further seems to play an important role in host defense against infections such as bacterial infections (Belaaouaj, 2002, *Microbes and infection* 4:1259-1264).

In an inflammatory response, levels of elastase activity can rise dramatically. Prolonged release of elastase can lead to tissue destruction, as the enzyme targets the destruction of a number of cytoskeleton-related proteins such as elastin, collagen and cytokeratin.

It was determined by the inventors that CFS can be diagnosed by assaying a patient sample (or host specimen) for elastase activity.

In the immune cells of patients with CFS, elastase activity is increased, directly correlating with the fragmentation of RNase L.

Surprisingly, this is not the case in the immune cells of patients with MS or RA. Samples of RA or MS patients contained RNase L protein fragments but exhibited normal (preferably below about 900, more preferably below about 700, most preferably below about 500 U/mg total protein) to moderately increased elastase activity (elastase activity between about 1,000 and about 2,000 U/mg total protein).

The utility of (intracellular) elastase as clinical marker for CFS is hereby demonstrated.

CFS, like MS and RA, is a syndrome, id est a disease of which the underlying disease mechanisms are not known. Syndromes are defined more or less arbitrarily by the observed constellations of symptoms and signs.

Certainly in the case of syndromes, diagnosis is by no means an error-free, objective fact.

The measuring of elastase activity levels present in cells helps the physician in the clinical decision process of a complex syndrome like CFS. It helps him in establishing a more sound diagnosis of CFS and aids him in his search for the most appropriate treatment.

The methods of the invention are particularly suited to confirm the presence of CFS in patients suspected to suffer from CFS, or in patients who have been previously diagnosed as fulfilling the diagnostic criteria for CFS for instance per the Centers for Disease Control and Prevention (CDC) guidelines of 1988.

The methods of the present invention are further suited to characterize CFS; to determine a CFS disease stage and/or its progression; to predict possible attacks; and/or to monitor the efficiency of a CFS therapeutic regimen.

The methods of the invention advantageously can allow for the conclusive diagnosis of CFS when the elastase assay of the invention is performed in combination with other tests (at least one second method), such as for instance an Rnase L fragmentation assay.

The methods of the invention advantageously allow to distinguish CFS from other like CICIDs like MS or RA. Such distinction is not possible when RNase L fragmentation alone is used as clinical marker.

Advantageously, the methods of the invention can thus be used to determine or to confirm that MS or RA activity is not present in a patient.

The elastase assays of the invention can further provide an assessment of the severity of immune cell dysfunction in CFS patients caused by the cleavage of RNase L by elastase activity.

A method of the invention for (adjunct) diagnosing of CFS comprises the step of measuring elastase activity in a patient sample, in particular in a PBMC (cytoplasmic) extract.

An embodiment of the invention concerns ex vivo or in vitro assays (methods and kits) for the above purposes.

"Measuring" implies amongst others determining the elastase activity, preferably quantifying or semi-quantifying said activity, so that elastase levels that are measured can be compared with a "range or amount of reference". From said comparison, an increase or decrease in elastase activity, or a stagnation of elastase activity can be determined.

An increase in elastase activity as compared to a "reference range" or "reference amount", can indicate the putative presence, the presence and/or the progression of CFS.

The absence of such an increase can indicate that the person in question is not suffering from CFS.

The absence of an increase can also indicate that CFS is not progressing, or that a therapeutic regimen is effective for the CFS patient.

A decrease in elastase activity can indicate a curing from CFS.

A "reference range" or "reference amount" can be the range or amount of elastase activity in general observed or expected for a healthy individual or group of individuals. In other cases (estimation of disease progress or of disease state), it can be the range or amount of elastase activity in general observed or expected for an individual or group of individuals characterized by a particular disease state.

A "normal range" or "normal amount" refers to a range or amount in general observed in "healthy patients", "healthy individuals" or "healthy controls".

The "amount" can refer to a mean value for a group of patients or individuals.

The term "determining a range or amount of reference" can imply that elastase activity is measured for a reference group and that a reference range or amount is derived from said measurements. The term can, however, also refer to the consultation of a reference list or table and the finding therein of the reference range or amount that matches with sex, age, disease state etc. of the individual or patient to diagnose.

Below, some preferred samples in which to measure elastase activity according to the invention are indicated.

Elastase is found in a number of cell types including pancreatic cells and leukocytes such as monocytes and neutrophils (lysosomal elastase, EC # 3.4.21.37, contained within the granules of neutrophils).

A statistically significant correlation ($R=0.92$) was observed between elastase enzymatic activity in peripheral blood mononuclear cells (PBMCs) from patients with CFS, and the amount (fraction) of 37-kDa RNase L fragments, a generally accepted measure of CFS disease activity.

In cytoplasmic protein extracts of PBMCs, elastase activity was significantly higher in CFS patients than in healthy controls.

In said PBMC protein extracts of CFS patients, 37-kDa RNase L fragments can be found. As mentioned above, the presence of this fragment indicates the presence of a CICID activity, like CFS activity.

Advantageously, samples in which to measure elastase activity according to the invention contain enzymatically active elastase (id est the active form of elastase).

According to an embodiment of the invention, the sample is one that is suspected to contain RNase L protein fragments and is suspected to have an increased elastase activity, whenever said patient is suffering from CFS.

A "sample" or "host specimen", in the present context, can be a cell and/or tissue derived sample such as a cytoplasmic extract. Preferably the sample is a blood (blood-derived) sample.

A preferred blood (blood-derived) sample is one that comprises primarily monocytes. By "primarily" is meant that the blood (blood-derived) sample or blood fraction used is depleted from neutrophils.

Preferably such sample contains less than about 10%, preferably less than about 5 to 6%, more preferably less than about 2%, most preferably less than about 1% neutrophils.

A most preferred sample is one derived from peripheral blood mononuclear cells (PBMCs), also referred to as a PBMC sample or PBMC fraction.

The PBMC fraction is the fraction of white blood cells containing mainly lymphocytes and monocytes. PBMCs consists (essentially) of lymphocytes and monocytes.

A preferred PBMC sample is one that contains less than about 10%, 9%, 8%, 7%, 6%, 5%, 4%, 3%, 2% or less than about 1% neutrophils. The latter are also referred to as 90, 91, 92, 93, 94, 95, 96, 97, 98 to 99% pure PBMC samples.

According to an embodiment of the invention, the method comprises the step of isolating peripheral blood mononuclear cells (PBMCs) as source of intracellular elastase and comprises the step of measuring the active elastase level in said cells. Preferably elastase activity is measured in cytoplasmic PBMC extracts.

An embodiment of the invention relates to the measuring of elastase activity present in monocytes.

In monocytes, elastase enzymatic activity is low (preferably below about 900, more preferably below about 700, most preferably below about 500 U/mg total protein) or moderately increased (elastase activity between about 1,000 and about 2,000 U/mg total protein) in samples or host specimens that are derived from healthy individuals, whereas this activity is sufficiently high in samples derived from diseased individuals, so that a clear-cut distinction can be made between healthy and diseased individuals.

In neutrophils, at the contrary, elastase levels are already very high in normal conditions, id est when a patient is not suffering from a CICID like CFS. Relative difference in elastase activity between diseased and healthy individuals or patients can, as such, be too low in neutrophils to guarantee a proper diagnosis.

By "diseased", in the present context, is meant that the individual is suffering from a CICID like CFS.

The term "healthy controls", "healthy patients" or "healthy individuals", in the present context, refers to patients or individuals that are not suffering from the disease to diagnose, in particular the CICID and more in particular CFS.

A "control patient" can be a "healthy patient" or a "diseased patient", depending on whether one wants to determine the presence/absence of CFS, the disease stage, the progression or possible curing from CFS (see infra).

Elastase activity levels measured in "control patients" are referred to as "control levels" or "reference levels".

A "patient" can be a mammal, but preferably is a human.

Proper "diagnosis" minimally implies that healthy and diseased individuals or patients can be easily distinguished.

It can further be advantageous that the disease stage, disease progression, the efficiency of a therapeutic regime etc. can also be determined and/or that the prediction of recurrence of possible attacks is possible.

Preferably, elastase enzymatic activity is measured by measuring the digestion of an elastase-substrate.

Antibodies that measure total amounts of elastase (both active and non-active forms) should not be used. Antibodies specific for the active form of elastase, however, can be used. By "specific" is meant that the antibody in question does not recognize the non-active form. An antibody can be a polyclonal or a monoclonal antibody or any antibody fragment that serves the purpose.

The elastase-substrate can be a substrate that is naturally present in the sample to assay. Alternatively, the substrate can be added to the reaction medium, id est to the sample.

Advantageously, an elastase-substrate selected from the group consisting of elastin, RNase L, cytokeratin 18, collagen, proteoglycan, thrombomodulin, cadoherins and fibronectin is used. These are examples of cellular protein substrates cleaved by elastase activity.

In fact any substrate that is recognized and cleaved by elastase, and preferably is elastase-specific, can be used.

A list of natural elastase-substrates and target cells of elastase is given in table I of Kawabata et al. (2002, *European J of Pharmacology* 451:1-10).

Advantageously, protease inhibitors of proteases other than elastase, which otherwise might interfere with the elastase measurement, are added to increase the sensitivity and/or selectivity of the test.

For instance, protease inhibitors can be added to impair those proteases that are able to recognize and cleave the elastase-substrate that is added to the reaction medium and/or that is present in the cells.

Alternatively, one can use an elastase-specific substrate id est a substrate that is cleaved by elastase only or that is cleaved only in very small, id est negligible, amounts by other proteases such as matrix metalloproteases.

Examples of inhibitors of interfering (serine) proteases include but are not limited to Aprotinin (Azouqahg-Oualane et al, 1992, *Thromb. Res.* 68:185), Chymostatin (Murakami et al, 1991, *Biochim. Biophys. Acta* 1079:279) 3,4-Dichloroisocoumarin (Harper et al, 1985, *Biochemistry* 24:1831), and Phenylmethylsulfonyl Fluoride (Chandg et al, 1992, *Biochem. Int.* 28:707).

When adding protease inhibitors while extracting intracellular elastase protein, care should be taken not to include elastase-specific inhibitors. They should preferably be removed and/or inactivated or impaired whenever present (for instance in some commercial mixtures), because their presence would otherwise result in incorrect levels being measured. Reversible elastase inhibitors can be added.

It is possible to use protease mixtures that comprise a reversible inhibitor of elastase (e.g. Alpha-1 Antitrypsin described by Spence et al, 1993, *Biochem. Med. Metab. Biol* 50:233) and an irreversible inhibitor of possibly interfering serine proteases (see e.g. European Patent Application EP0528525).

When a method according to the invention indicates or reveals changes in elastase activity, it can be advantageous to confirm a diagnosis made on the basis of elastase levels via other means, id est via a further or second (standard) methods or assay.

This can be particularly advantageous in case of presumed false positives or negatives.

Other means can include the observation of clinical symptoms (a physical exam), the examination of biopsies, taking of X-rays, MRI imaging, taking of scans, the performing of known diagnostic tests for said disease and/or pathology etc.

An example of a recognized or standard test/assay for CFS diagnosis is one that comprises the step of assaying a patient sample for the presence of low molecular weight (LMW) RNase L fragments, like the 37-kDa fragment.

One can as such assay for the presence of at least one LMW RNase L fragment, like the 37-kDa fragment.

Alternatively, one can determine the relative amount of LMW RNase L fragments compared to native RNase L (non-cleaved form with a molecular weight of about 80 to about 83 kDa, also referred to as high molecular weight (HMW) RNase L).

One can also determine the relative amount of LMW RNase L fragments compared to the total amount of RNase L species (native RNase L plus its fragments).

These relative amounts can be expressed as fractions and/or as ratios.

In the present context, ratio means [[LMW RNase L/HMW RNase L]×10] and fraction means [LMW RNase L/(LMW RNase L+HMW RNase L)]. Fractions can be expressed as percentages.

RNase L assays are often based on assaying the presence of 37-kDa RNase L fragments.

One can, however, also look at the presence of other RNase L fragments (id est fragments other than the 37-kDa fragment), as long as there is an undeniable link with the presence or absence of a CICID like CFS, or with a certain disease stage thereof (see infra).

Measured elastase activity levels can also be used as such.

In males, an absolute level of at least about 700, about 800, about 900 or about 1,000 units/mg (total) protein, preferably at least about 1,200, about 1,500, about 1,750, about 1,900, about 2,000 units/mg protein, more preferably of at least about 2,500, about 3,000, about 4,000, about 5,000, about 6,000, about 7,000 units/mg protein, in cytoplasmic protein extracts of PBMCs is indicating the presence of CFS. An elastase activity of up to about 10,000 to about 12,000 units/mg protein can be measured in males.

In females, an (active) elastase amount of at least about 650, about 700, about 800, about 870, about 900 or about 1,000 units/mg (total) protein, preferably at least about 1,200, about 1,500, about 1,750, about 1,900, about 2,000 units/mg protein, more preferably of at least about 2,500, about 3,000, about 4,000, about 5,000, about 6,000, about 7,000 units/mg protein, in cytoplasmic protein extracts of PBMCs is indicating the presence of CFS. An elastase activity of up to about 10,000 to about 12,000 units/mg protein can be measured in females.

In terms of a relative difference between healthy and diseased individuals, a relative difference of at least 1.5, preferably at least twice, most preferably at least thrice, four times or five times the normal (i.e., healthy) range or amount is indicating the presence of CFS. In some cases, a relative difference of about 6, 7, 8, 9, 10, 12, 14, 16, 18 to even about 20 times the normal (i.e., healthy) range or amount can be observed.

For populations and patient groups other than the one examined here (different race, age, etc.), thresholds can of course vary.

The present invention relates to methods to determine and measure elastase activity present in cells, preferably the activity present in monocytes.

According to an embodiment of the invention, the method comprises the steps of isolating the appropriate patient sample and then measuring elastase activity in cells or tissues of said sample.

Advantageously, elastase activity is measured in a PBMC sample (that contains monocytes) such as a 95% pure PBMC sample.

The present invention further relates to kits for performing any of the above methods, said kit comprising at least means for isolating PBMCs and/or at least one elastase-substrate.

DETAILED DESCRIPTION OF THE INVENTION

Figure 1:
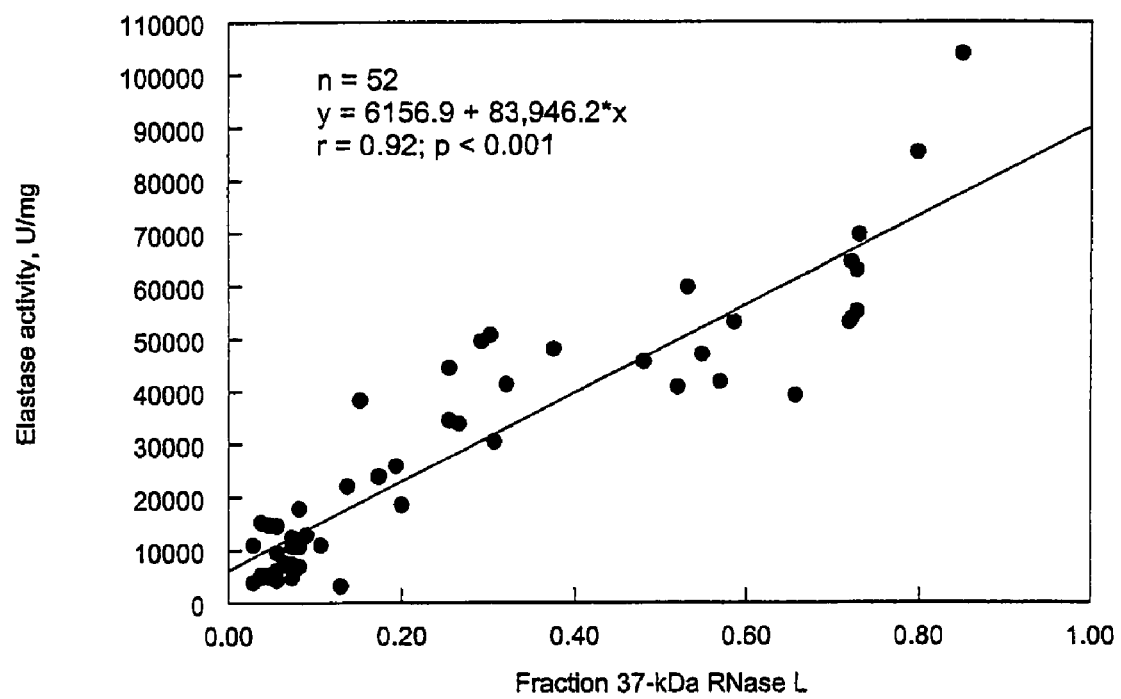
FIG. 1 represents a graph measuring the correlation between the amount (U/mg total protein) of elastase enzymatic activity present in peripheral blood mononuclear cells (PBMCs) directly, and the fragmentation observed of one of its intracellular protein substrates (RNase L protein) in specimens from patients with clinically documented Chronic Fatigue Syndrome (CFS). n=52. y=6156.9+83,946.2*x. r=0.92. p<0.001. RNase L fragmentation in this Figure is expressed as the fraction of 37-kDa RNase L fragments, a generally accepted measure of CFS disease activity.
Figure 2:
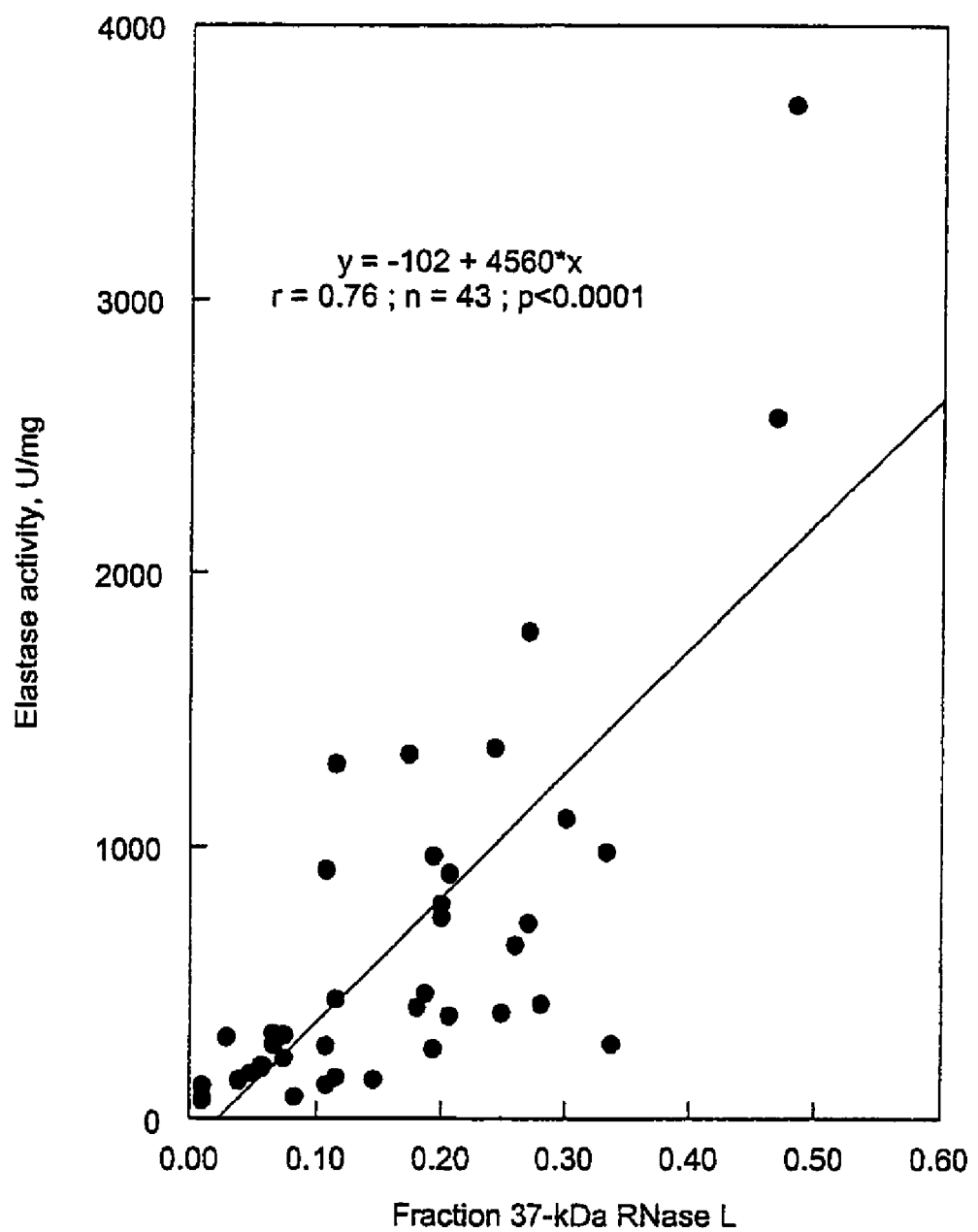
FIG. 2 represents a graph measuring the correlation between the amount (U/mg total protein) of elastase enzymatic activity present in peripheral blood mononuclear cells (PBMCs) directly, and the fragmentation observed of one of its intracellular protein substrates (native RNase L protein) in specimens from healthy controls. n=43. y=−102+4560*x. r=0.76. p<0.0001.

Before the present invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications that might be used in connection with the presently described invention.

In the methods according to the present invention, elastase enzymatic activity is measured in a sample of a patient, preferably a patient suspected to suffer from CFS.

As part of the diagnosis, one can also evaluate the subject or patient for other symptoms of the disease of interest that is to be diagnosed. For example, where the disease of interest is CFS, clinical symptoms of interest include: fatigue of six months or longer that causes a reduction in effort of greater than 50 percent of normal output, arthralgia, myalgia, sore throat accompanied by swollen glands, cognitive dysfunction (e.g. memory loss); and the like. For MS, clinical symptoms include: weakness of the limbs; sensory symptoms, e.g. paresthesia or hypesthesia; ataxia; optic neuritis; diplopia; trigeminal neuralgia; facial paralysis; vertigo; urinary or bowel movement abnormalities; and cognitive dysfunction, e.g., memory loss, impaired attention, problem-solving difficulties, slowed information processing, and difficulty in shifting between cognitive tasks. The presence of one or more of the above symptoms can be used to identify subjects suspected of suffering from CFS or MS, respectively. Other assays can also be employed, including MRI imaging, the oligoclonal band assay described in greater detail infra, etc. For RA, clinical symptoms include: inflammation of the membrane lining the joint, which causes pain, stiffness, warmth, redness and swelling.

When the results obtained by a method for CFS according to the invention is negative, but RNase L fragments like the 37-kDA fragment are found, this can indicate the presence of MS or RA activity.

A preferred sample in which to measure elastase levels according to the invention is a PBMC derived sample, generally a fluid PBMC derived sample. Any convenient methodology for producing a fluid PBMC sample can be employed. The fluid PBMC derived sample can for instance be prepared by: (a) separating PBMCs from whole blood, i.e. collecting PBMCs, e.g. by centrifugation (such as by Ficoll-Hypaque density gradient centrifugation); (b) disrupting the collected cells, e.g. by contacting with a lysing buffer; (c) and removing the resultant cellular debris to obtain a cell-free extract, e.g. by centrifugation. Representative means for producing a suitable fluid PBMC derived sample, i.e. a fluid PBMC extract, are disclosed in e.g. WO 98/15646, U.S. Pat. No. 5,985,565 and Suhadolnik et al. (1983, *Biochemistry* 22:4153-4158). These references are incorporated by reference herein, with respect to the preparation of cytoplasmic PBMC extracts.

Once the patient derived sample is obtained, it is assayed for an increase or decrease in elastase enzymatic activity, and this preferably by using a direct assay. The test can be semi-quantitative or quantitative, and is usually at least semi-quantitative (id est, not just qualitative).

Elastase enzyme in pure form can be used as positive control in the above methods and tests. The use of positive controls, and various known dilutions thereof, allows for the quantification of the methods and tests, for instance by comparing detection signals with a detection signal of a fixed and known amount of reference material.

Preferred assays are those in which active elastase cleaves a substrate to generate a visible end product such as a fluorescent, a phosphorescent, colored or otherwise labeled reaction product.

Synthetic calorimetric and/or fluorogenic elastase-substrates can be purchased from several companies (e.g. elastase-substrates I-VIII from Calbiochem, US).

A protocol of particular interest includes one performed with the following commercially available assay kits: EnzCheck® Elastase Assay kit (Cat. No. E-12055; Molecular Probes, Inc., Eugene, Oreg.).

The EnzCheck® Elastase Assay kit contains DQ™ elastin—soluble bovine neck ligament elastin that has been labeled with BODIPY®FL dye such that the conjugate can be digested to yield highly fluorescence fragments. The resulting increase in fluorescence can be monitored with a fluorescence microplate reader.

Any other protein known to be a substrate for elastase enzymatic activity can be used, such as for instance RNase L protein.

Elastase enzymatic activity can thus be determined by assaying for the presence (or absence) of low molecular weight (LMW) RNase L protein species or fragments.

One can as such assay for the presence of native RNase L protein and total RNase L protein species. From the relative amount of native RNase L protein to total RNase L protein species in a sample, the presence of low molecular weight RNase L protein fragments can then be determined.

Information on the size, molecular weight and activity of native RNase L, its high and low molecular weight fragments can be found in International Patent Applications WO 00/65086, WO 02/15929 and in U.S. Pat. No. 5,985,565.

The following can for instance be used to express presence (or absence) of LMW RNase L fragments: relative amounts of the various RNase L protein species in the sample to each other [e.g. the relative amount of native or high molecular weight RNase L protein to the total amount of RNase L protein species], patterns, fractions or ratios of the various RNase L protein species.

An explanation of the terms "relative amounts", "pattern" and "ratio" can be found in International Patent Application WO 02/15929, which is specifically incorporated by reference herein with respect to these terms.

The amount of native RNase L protein and lower (low) molecular weight RNase L protein fragments can for instance be measured by using the 2'-5'A binding assay as described in Charachon et al. (1990, *Biochemistry* 29:2550-2556). As such, the assay employed may or may not also include a determination of the amount of native or full length RNase L protein, i.e. RNase L protein having a molecular weight of about 80 to about 83 kDa, in the sample.

Any convenient assay or assay protocol, however, can be employed to measure RNase L protein fragmentation (see infra). Suitable assays that can be employed include antibody-based assays, e.g., Western blot assays, immunoassays (sandwich-type, competitive, or other), such as those described in the experimental section infra, and as described in WO 02/15929.

Antibody based assays require the use of antibodies specific for the RNase L protein fragments, for native RNase L protein and/or for both native and fragmented RNase L protein.

Antibody based assays may be direct assays, i.e. assays which employ antibodies specific for low molecular weight RNase L protein fragments. Alternatively, the assays may be indirect assays, i.e. those which detect native RNase L protein and total amounts of RNase L protein species in a sample, from which then the amount of cleaved RNase L can be derived.

RNase L specific antibodies are commercially available. International patent application WO 02/15929 describes three RNase L fragments that are found in chronic immune diseased individuals. These fragments can be used to raise antibodies specific for low molecular weight RNase L protein fragments that do not recognize native RNase L. Techniques for raising antibodies and for selecting the appropriate specific antibodies are well known in the art (see e.g. *Antibodies: A Laboratory Manual*, E. Harlow and D. Lane (eds.), Cold Spring Harbor Laboratory Press, NY, 1988, 726 pp.; *Immunochemistry in Practice*, 3rd ed., P. Johnstone and R. Thorpe (eds.), *Blackwell Science Ltd.*, 1996, 384 pp.)

Other suitable assays for detecting RNase L proteins include (1) the core-cellulose assay, as described in Silverman et al. (1985, *Anal. Biochem.* 144: 450-460); (2) the ribosomal cleavage assay, as described in Suhadolnik et al. (1994, *Clin. Infect. Dis.* 18:S96-S 104); (3) assaying for the hydrolysis of a labeled RNase L substrate, e.g. poly(U)-3'-[12p] pCp in the presence of p3A3; (4) the photolabeling/immunoprecipitation/fractionation assay, as described in Suhadolnik et al (1997, *J Interferon Cytokine Res.* 17: 377-85) and the like. Each of the above assays is further described in International Patent Application WO 98/15646, the disclosure of which is herein specifically incorporated by reference.

Assays for the determination of RNase L fragmentation can for instance be used as direct measure of elastase activity.

They can also be used to complement any results of the elastase assays of the invention, for instance to complement confirm and/or to evaluate elastase activity levels measured from elastin digestion.

In this case, the RNase L assay is an "additional assay", a "second (standard) assay", a "further assay" or "assay ran in parallel".

In a preferred embodiment of the invention, accurate diagnosis of CFS involves comparing the elastase activity levels obtained to predetermined values or reference values, which provide information about CFS in the host or patient. For example, a list or table of values can be consulted, where the list or table comprises representative values for the levels of elastase enzymatic activity found in patients that are suffering from CFS. The values for the latter are referred to as disease state levels or numbers. Preferably also reference values for individuals and/or groups not suffering from CFS (the so-called normal values for healthy or normal individuals and/or groups) are contained herein. Preferably the reference table or list includes representative values for subgroups according to sex, age etc.

The values can be presented in numerical format, in pictorial format (i.e., fluorescent scans) and the like.

A reference list or table can also be used to characterize CFS, i.e. to provide more information than just the presence or absence of CFS. Information can for instance be obtained on the disease state, progression thereof, the relapse, the occurrence of attacks, etc (see below). Reference tables or lists in this case preferably contain reference levels for patients in a certain stage or certain stages of the disease.

By comparing actual values with values earlier measured for a given patient, a comparison of the disease state over time can be made.

Some drugs may or can have an effect on intracellular elastase activity. For instance they may reduce or significantly suppress elastase activity, which may affect correct diagnosis. To reduce to the minimum false negatives due to that, it can be advantageous to repeat the elastase assay, or to perform the assay, at a moment the patient is not taking these drugs and the effects of such drugs have worn off.

The terms "characterization of a disease", "confirmation of diagnosis", "determination of a disease stage", of "disease progression", the "prediction of attacks" and the "monitoring of a therapeutic regimen" are as described and explained in International Patent Application WO 00/65086.

Briefly, characterization of disease activity yields information concerning CFS progression (e.g. acceleration or slowing down) in the patient. Elastase activity levels observed at the initial characterization date (day 0) can herein be employed as baseline values to evaluate subsequent testings, e.g. at some time following the initial testing, e.g. 3 months later.

If elastase activity decreases or stagnates in subsequent testings, this indicates that the disease is not progressing. An increase indicates that CFS is progressing in severity.

The characterization data obtained can also be used to determine whether a particular therapeutic regimen is having positive effects with respect to the progression of CFS. For example, at various time periods during the course of treatment, the elastase methods of the invention can be performed to obtain a reading of the actual intracellular elastase activity. If elastase activity is increasing, this indicates that the treatment regimen is not having the desired effect. A decrease indicates that the treatment regimen is working.

In yet other embodiments, the characterization data obtained may or can be used to predict when a CFS attack may occur. In this embodiment, the characterization data are compared to reference values, where some of the reference values correlate to the occurrence of an attack.

The present invention further relates to kits for carrying out the assays and methods of the invention. Said kits include all the necessary means to assay for elastase enzymatic activity.

The kit components advantageously include, but are not limited to: devices comprising the same; members of a signal producing system, such as antibodies, enzyme substrates, and the like; various buffers for use in carrying out the detection assays of the invention; and the like; a range of standard concentrations of elastase enzyme and/or a single concentration elastase enzyme that can be diluted to provide a standard range of concentrations, inhibitors and the like.

The kits advantageously further include one or more reagents necessary for preparation of the patient derived sample, such as heparin, Ficoll-Hypaque, red blood cell lysing buffer, and the like to prepare PBMC samples.

In addition, the kits of the invention advantageously include one or more components employed in fractionation of the sample, such as an electrophoretic medium or precursors thereof, e.g. dried precursors of polyacrylamide gels, one or more buffer mediums or components thereof, and the like.

In most embodiments, the kits further include at least an information storage and presentation medium that contains reference data with which assay results can be compared in order to diagnose and/or characterize a particular disease or pathology linked with altered active elastase levels.

Such information can include various values of the levels of elastase enzymatic activity in one or more types of a patient specimen (e.g. serum-derived versus PBMC-derived elastase enzymatic activity) and/or disease states and relates these values to the presence or absence of said disease and/or the activity of the disease in a host.

The information storage and presentation medium can be in any convenient form, such as that of printed information on a package insert, an electronic file present on an electronic storage medium, e.g. a magnetic disk, CD-ROM, and the like. In yet other embodiments, the kits can include alternative means for obtaining reference data, e.g. a web site for obtaining the reference data "on-line." The kits advantageously further include means for obtaining the patient sample, e.g. a syringe.

The kits of the invention further typically can include instructions for carrying out the methods of the invention, where these instructions can be present on a package insert and/or the packaging of the kit. Finally, the kit can further include one or more reagents from an additional biochemical assay, which is used to detect and/or diagnose the disease or pathology of interest.

The following examples are offered by way of illustration and not by way of limitation.

EXAMPLES

Example 1

In vitro Analysis of Elastase Enzyme Activity and Comparison to Levels of Native RNase L Protein Fragmentation in Peripheral Blood Mononuclear Cells from Patients with CICIDs CFS study subjects were patients who had been previously diagnosed as fulfilling the diagnostic criteria for CFS per the Centers for Disease Control and Prevention (CDC) guidelines of 1988 (Holmes et al. (1988), *Ann. Intern. Med.* 108:387-389). Level of fatigue was assessed using the Karnofsky Performance Score (KPS) criteria. Patients were selected from a medical practice in Brussels, Belgium.

MS study subjects were selected from a medical practice in Overpelt, Belgium. RA subjects were selected from medical practices in Brussels, Belgium, and Johannesburg, South Africa. At the time of blood sampling, patient symptoms were evaluated and recorded.

A. Procedures

1. Blood Sample and Shipment Requirements

About 20 mLs of whole blood suffice for the measuring of elastase activity as described below. The preferred anticoagulant is Acid Citrate Dextrose (ACD). A suitable alternative to ACD is to use cell preparation tubes (CPT™) containing a cell separation medium.

If shipped, the blood sample must be shipped at ambient (room) temperature by overnight express courier for delivery the next day. Blood specimens that are more than one day in transport are not directly usable.

2. Preparation of a Mononuclear Cell Pellet

Peripheral blood mononuclear cells (PBMCs) were separated from heparinized blood (30 mLs) by Ficoll-Hypaque density gradient centrifugation. The blood was layered onto 20 mLs of Ficoll-Hypaque (Boyum (1968), *Scandinavian Journal of Clinical Laboratory Investigation,* 97:101-109) at a density of 1.077 g/mL at 20° C. and centrifuged for 30 minutes at 500×g. The PBMC layer was removed and washed once with 5 volumes of phosphate buffered saline (PBS). The cells were then resuspended in 5 mLs of red blood cell lysing buffer (155 mM $NH_4Cl$, 10 mM $NaHCO_3$, 0.1 mM EDTA, pH 7.4), kept on ice for 5 minutes, then centrifuged for 5 minutes at 500×g. The resultant cell pellet was washed once with 15 mLs of PBS and centrifuged for 5 minutes at 500×g. The resultant pellet was then stored at −70° C. until the protein extraction procedure could be performed. An about 95% pure PBMC sample is obtained.

3. Extraction of Cytoplasmic Proteins from the Mononuclear Cell Pellet

To extract the proteins from the cell pellet, PBMCs were resuspended in a volume approximately 5-10 times the packed cell volume in the extract buffer (10 mM HEPES, pH 7.6, 90 mM KCl, 1.5 mM $Mg(OAc)_2$, 0.5% non-ionic detergent (such as Nonidet P-40 or Igepal CA-630, Sigma Chemical Corporation)). The extract buffer also contained a mixture of protease inhibitors to help stabilize the extract and impeded the action of proteases. One such commercially available mixture is the MiniComplete protease inhibitor cocktail (Boehringer-Mannheim) containing aprotinin, leupeptin, pefabloc-SC and EDTA.

The extraction procedure was performed at about 2 to about 4 degrees C., holding the cell pellet-extraction buffer in ice water or on wet ice for about 5 minutes. The cell pellet-buffer mix was then vortexed at medium speed for about 2 minutes at room temperature to ensure complete solubilization of the cytoplasmic membranes. The cell pellet-buffer mix was then placed at about 2 to about 4 degrees C. for an additional 5 minutes. The final step was to centrifuge the cell pellet-buffer mix at high speed in a microcentrifuge (16,000× g) for about 2 minutes. The supernatant containing the proteins of interest was collected and the cell pellet was discarded. All cell extracts were stored at −70° C. until further analysis could be performed.

Quantification of protein in the patient cell extracts was performed using a standard commercially available procedure of a modified Bradford method (Bio-Rad Laboratories) following the manufacturer's recommended procedure.

4. Quantification of 2'-5'A Binding Proteins

Analysis of LMW and HMW RNase L Proteins was performed using a radiolabeled 2'5'A trimer and SDS-PAGE as described by the method of Charachon et al. (1990), Biochemistry 29:2550-2556. Briefly, 2-5A trimer was radiolabeled by the ligation of $^{32}$P-pCp to the 3' end (method of Charachon). After removal of the 3' terminal phosphate by treatment with bacterial alkaline phosphatase, the 3' ribose residue of pC was oxidized with sodium metaperiodate (10 mM final concentration, pH 4.75) for one hour at 4° C. to form 2-5A-$^{32}$P—C—OX. This reaction mixture was subsequently equilibrated to pH 8.0 by the addition of NaOH. This oxidized molecule was used as the radiolabel in all subsequent reactions for RNase L protein analysis (referred to below as radiolabeled 2-5A).

To demonstrate the binding of 2-5A by rRNase L protein and fragments thereof, the radiolabeled 2-5A was incubated with 0.1 microgram of elastase-digested recombinant RNase L protein at about 2 to about 4 degrees C. for about 15 minutes to allow the radiolabeled 2-5A to interact with any 2-5A-binding proteins present, such as the full length rRNase L protein and all lower molecular weight species still retaining the 2-5A binding site. The 2-5A radiolabel was then covalently attached to the rRNase L protein and all lower molecular weight species present still retaining the binding site by the addition of cyanoborohydride (20 mM in 100 mM phosphate buffer, pH 8.0). The reduction reaction was allowed to occur for about 20 minutes at room temperature. SDS-PAGE sample buffer, including a tracking dye, was added to the samples and all samples were incubated at about 95° C. for about 5 minutes under reducing conditions.

The samples were then subjected to standard SDS-polyacrylamide gel electrophoresis using a 4 percent stacking gel and a 10 percent separating gel (Bisbal et al. (1989), Euro. J. Biochem. 179:595-602). Also included in the first lane of each gel was a molecular weight marker, pre-stained to be visible as it migrated during the course of electrophoresis (Bio-Rad Laboratories). The gel was electrophoresed until the tracking dye had migrated to the bottom of the gel (approximately 5 hours at a constant current of 30 mAmps). The gel was then dried and subjected to autoradiography (Bio-Rad Laboratories FX Imager).

The autoradiographs were then analyzed by densitometry, and quantification of any and all RNase L protein species present was performed using specialized software (Quantity One from Bio-Rad Laboratories).

5. Quantification of Elastase Activity in Cytoplasmic Protein Extracts

Elastase enzymatic activity was measured using a commercially available kit (EnzCheck® Elastase Assay Kit, Cat. No. E-102056, Molecular Probes, Inc., Eugene, Oreg., USA) according to the manufacturers instructions. Briefly, each cytoplasmic protein extract to be measured for elastase enzymatic activity was diluted to a final protein concentration of 0.5 micrograms per microliter (ug/uL) in 1× kit buffer (10 mM Tris-HCl, pH 7.5). To quantify the level of elastase enzymatic activity, a standard curve was prepared using pancreatic elastase (positive control provided in the kit), diluted with the 1× buffer to a variety of known concentrations. The 1× buffer was used alone as a negative or background control (i.e., no elastase enzymatic activity).

The stock solution of substrate for elastase enzymatic activity is the protein elastin that has been heavily labeled with a fluorescent dye to quench the fluorescence; thus any enzymatic activity that digests the substrate will release fluorescence into the medium and increase the amount of fluorescence. To perform the assay, 150 microliters of diluted substrate (1:300 dilution in 1× kit buffer) was added to each well of a 96 well flat-bottomed plate (Nunc, Life Technologies, Gaithersburg, Md., USA), followed by the addition of 50 microliters of specimen, standard or control. Each specimen, standard and control was assayed in triplicate. The plate was incubated at about 37 degrees C. in a humidified atmosphere for about two hours. The fluorescent intensity was then measured at 515 nm using a laser scanner with specialized software (Quantity One from Bio-Rad Laboratories). Actual elastase activity levels or elastase enzymatic activity was determined by interpolating values from the equation of the curve (fluorescence versus elastase concentration) after appropriate correction for the dilutions made. Each sample was corrected for background fluorescence by subtracting the value derived from the no-enzyme control (blank).

B. Results

FIG. 1 demonstrates that there is a statistically significant correlation (R=0.92) between elastase enzymatic activity (U/mg) in PBMCs from patients with CFS and the amount (fraction) of 37-kDa RNase L fragments, a generally accepted measure of CFS disease activity. Such a correlation is also found in healthy individuals (R=0.76).

Figure 3:
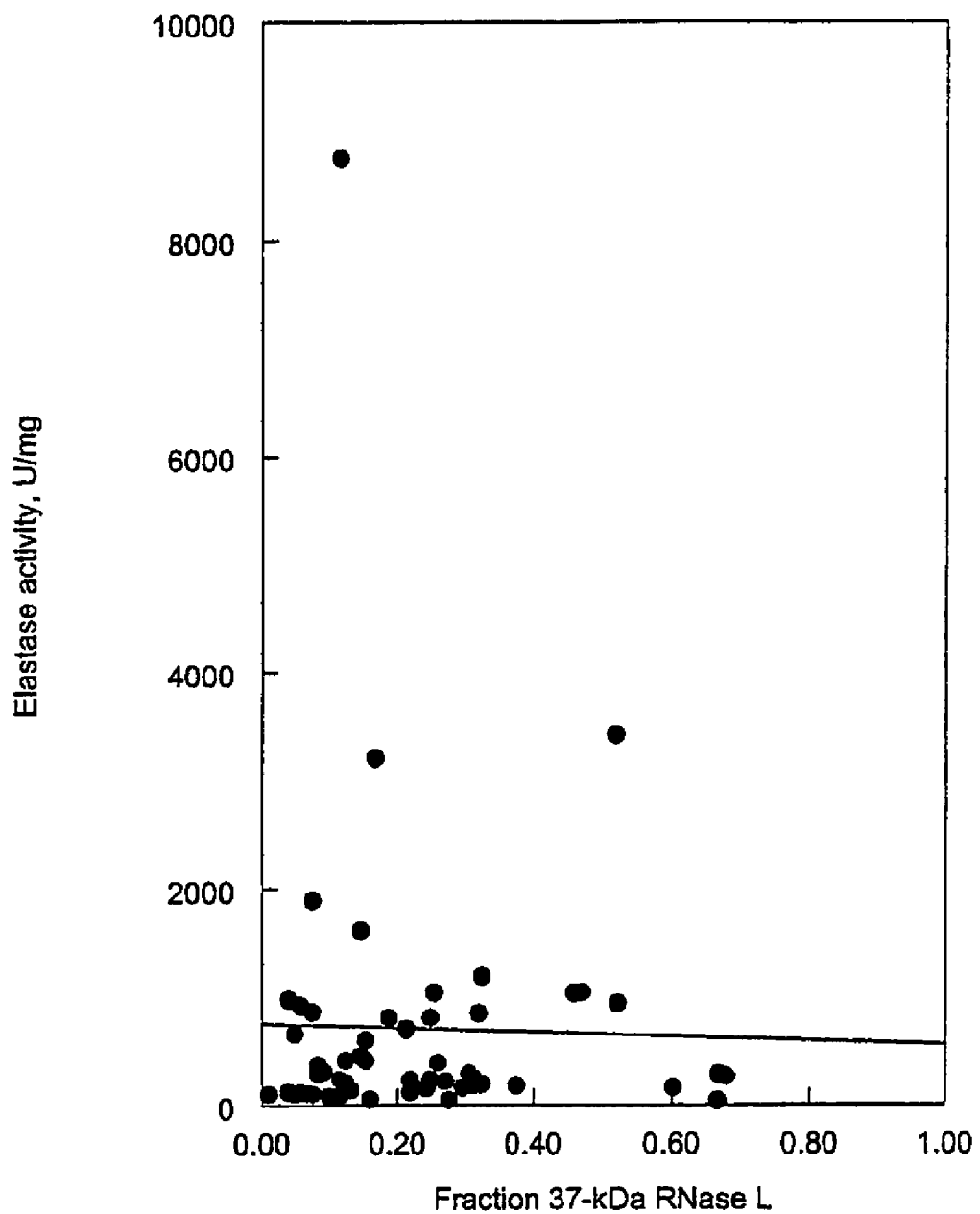
FIG. 3 represents a graph measuring the correlation between the amount (U/mg total protein) of elastase enzymatic activity present in peripheral blood mononuclear cells (PBMCs) directly, and the fragmentation observed of one of its intracellular protein substrates (native RNase L protein) in specimens from patients with clinically documented Multiple Sclerosis (MS).
Figure 4:
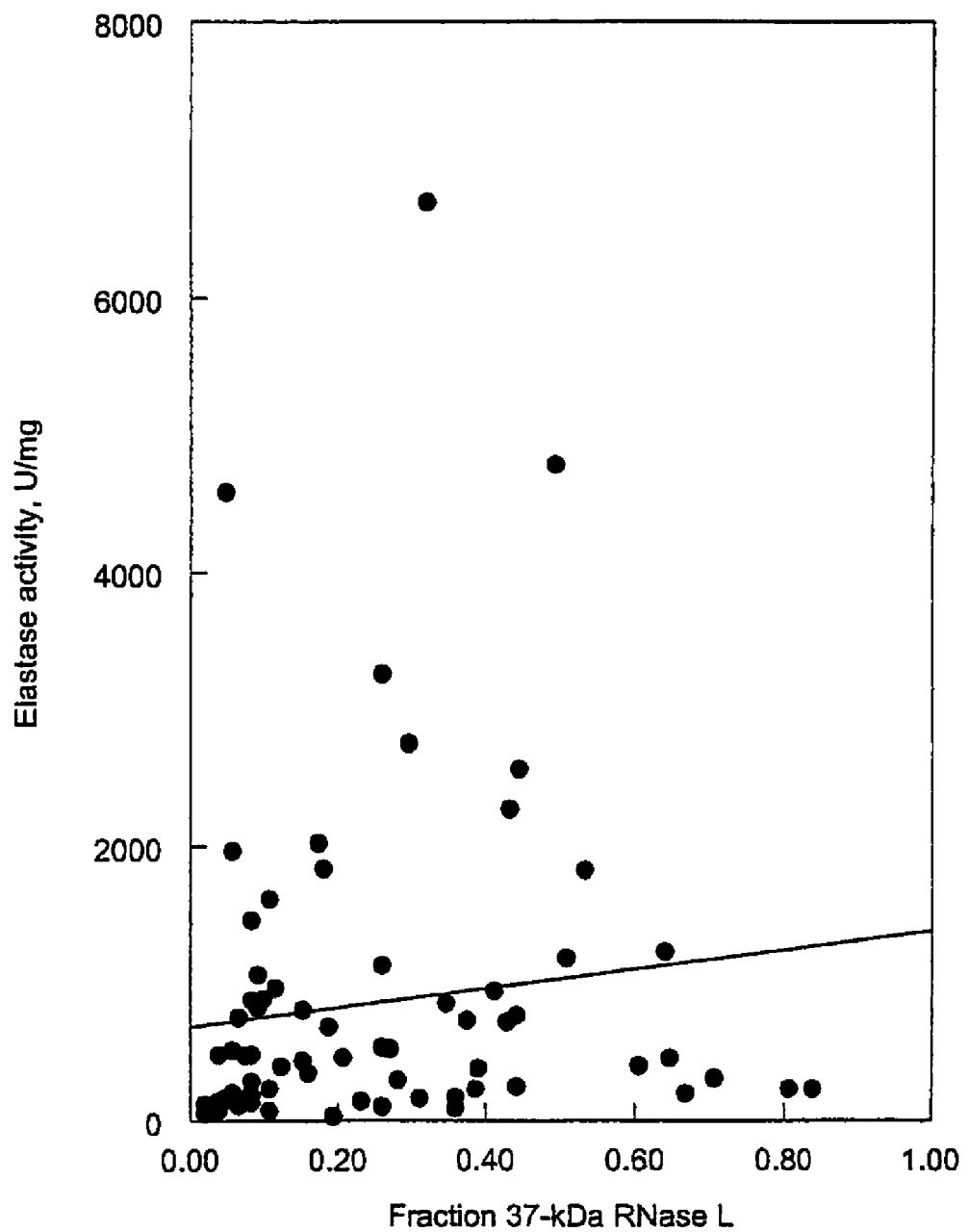
FIG. 4 represents a graph measuring the correlation between the amount (U/mg total protein) of elastase enzymatic activity present in peripheral blood mononuclear cells (PBMCs) directly, and the fragmentation observed of one of its intracellular protein substrates (native RNase L protein) in specimens from patients with clinically documented Rheumatoid Arthritis (RA).

FIGS. 3 and 4 demonstrates that no such statistical correlation exists for MS or RA.

The reader is appreciated to note that the unit value (U/mg) of the y-axes is of a different scale in each figure when comparing one result to the next.

The above clearly demonstrates the utility of elastase activity as clinical marker for CFS.

The invention claimed is:

1. A method for diagnosing chronic fatigue syndrome (CFS) comprising measuring elastase activity in a patient sample and comparing a level of elastase activity to a reference, wherein an increased level of elastase activity relative to a reference sample indicates the presence of CFS.

2. The method according to claim 1, which is an adjunct method for diagnosing CFS.

3. The method according to claim 1 or 2, wherein said sample contains 10% or less of neutrophils.

4. The method according to claim 1, wherein said sample is a peripheral blood mononuclear cell (PBMC) sample.

5. The method according to claim 4, wherein said sample comprises more than 90% PBMCs.

6. The method according to claim 1, wherein said measuring comprises measuring elastase activity present in monocytes.

7. The method according to claim 1, further comprising the steps of
   (a) determining the range or amount of reference elastase activity
   (b) comparing said elastase activity measured to said range or amount of reference
   (c) determining from step (b) the putative presence, the presence and/or the progression of CFS.

8. The method according to claim 1, wherein a relative difference of at least twice, preferably at least thrice the normal range or amount for elastase activity is indicating the presence of CFS.

9. The method according to claim 1, wherein an absolute elastase activity level in PBMCs of at least about 1,000 units/mg protein is indicating the presence of CFS in a male patient.

10. The method according to claim 1, wherein an absolute elastase activity level in PBMCs of at least about 900 units/mg protein is indicating the presence of CFS in a female patient.

11. The method according to claim 1, wherein said measuring comprises measuring digestion of an elastase-substrate.

12. The method according to claim 11, wherein said substrate is added to said sample.

13. The method according to claim 11 or 12, wherein said substrate is selected from the group consisting of elastin, RNase L, cytokeratin 18, collagen, proteoglycan, thrornbomodulin, cadoherins and fibronectin.

14. The method according to claim 1, wherein protease inhibitors are added to said sample to inhibit interfering serine proteases.

15. The method according to claim 1, further comprising the step of comparing the results obtained by a method according to claim 1 with those obtained by a control method.

16. The method according to claim 15, wherein said second (standard) method comprises the step of assaying a patient sample for the presence of low molecular weight RNase L fragments.

* * * * *